US011862312B2

(12) United States Patent
Gurumoorthy

(10) Patent No.: US 11,862,312 B2
(45) Date of Patent: Jan. 2, 2024

(54) SYSTEMS, METHODS, AND DEVICES FOR SLEEP INTERVENTION QUALITY ASSESSMENT

(71) Applicant: StimScience Inc., Berkeley, CA (US)

(72) Inventor: Ram Gurumoorthy, Lafayette, CA (US)

(73) Assignee: STIMSCIENCE INC., Berkeley, CA (US)

( * ) Notice: Subject to any disclaimer, the term of this patent is extended or adjusted under 35 U.S.C. 154(b) by 0 days.

(21) Appl. No.: 17/000,113

(22) Filed: Aug. 21, 2020

(65) Prior Publication Data
US 2022/0059201 A1 Feb. 24, 2022

(51) Int. Cl.
G16H 20/00 (2018.01)
G16H 15/00 (2018.01)

(52) U.S. Cl.
CPC ............. *G16H 20/00* (2018.01); *G16H 15/00* (2018.01)

(58) Field of Classification Search
CPC ........ G16H 20/00; G16H 15/00; G16H 20/40; G16H 50/30; G16H 50/20; A61B 5/00; A61B 5/0205; A61B 5/02; A61B 5/04; A61B 5/05; A61B 5/024; A61B 5/0476; A61B 5/0478; G06F 3/0482; H04L 67/12; A61N 1/00
USPC ....................................................... 705/2, 3
See application file for complete search history.

(56) References Cited

U.S. PATENT DOCUMENTS

| 2007/0123758 A1* | 5/2007 | Miesel .............. A61M 5/14276 |
| | | 600/301 |
| 2007/0129769 A1 | 6/2007 | Bourget et al. |
| 2008/0004904 A1 | 1/2008 | Tran |
| 2008/0052126 A1 | 2/2008 | Sasai et al. |

(Continued)

FOREIGN PATENT DOCUMENTS

| EP | 3958275 A1 | 2/2022 |
| EP | 3960071 A1 | 3/2022 |
| WO | WO-2016110804 A1 * | 7/2016 ............. A61B 5/024 |

OTHER PUBLICATIONS

European Application Serial No. 21192256.2, Search Report dated Feb. 2, 2022, 11 pgs.

(Continued)

*Primary Examiner* — Mamon Obeid
*Assistant Examiner* — Alaaeldin M Elshaer
(74) *Attorney, Agent, or Firm* — SCHWEGMAN LUNDBERG & WOESSNER, P.A.

(57) ABSTRACT

Provided are systems, methods, and devices for sleep intervention quality assessment. Methods include receiving measurement data from a plurality of data sources, the measurement data comprising a plurality of measurements of biological parameters of a user before and after a sleep intervention, and receiving treatment data comprising one or more treatment parameters associated with the sleep intervention. Methods further include generating, using one or more processors, a plurality of quality assessment metrics based on the received measurement data, the plurality of quality assessment metrics being generated based, at least in part, on a comparison of the plurality of measurements of biological parameters before and after the sleep intervention, and generating a report based, at least in part, on the plurality of quality assessment metrics.

19 Claims, 6 Drawing Sheets

(56) References Cited

U.S. PATENT DOCUMENTS

| | | | |
|---|---|---|---|
| 2013/0054215 A1 | 2/2013 | Stubna et al. | |
| 2013/0131464 A1* | 5/2013 | Westbrook | A61B 5/6814 600/301 |
| 2013/0303837 A1* | 11/2013 | Berka | A61B 5/389 600/27 |
| 2014/0006055 A1 | 1/2014 | Seraly et al. | |
| 2014/0184608 A1 | 7/2014 | Robb | |
| 2017/0000970 A1 | 1/2017 | Molina et al. | |
| 2017/0116373 A1 | 4/2017 | Ginsburg et al. | |
| 2018/0043182 A1 | 2/2018 | Wu et al. | |
| 2018/0289314 A1 | 10/2018 | Reifman et al. | |
| 2018/0325385 A1 | 11/2018 | Deterding et al. | |
| 2019/0099582 A1 | 4/2019 | Crow et al. | |
| 2019/0126033 A1 | 5/2019 | Pradeep | |
| 2019/0192069 A1 | 6/2019 | Garcia-Molina et al. | |
| 2020/0155061 A1 | 5/2020 | Pradeep | |
| 2020/0346017 A1 | 11/2020 | Caparso et al. | |
| 2022/0059208 A1 | 2/2022 | Gurumoorthy | |

OTHER PUBLICATIONS

U.S. Appl. No. 17/000,218, Final Office Action dated Jul. 29, 2022, 22 pgs.

U.S. Appl. No. 17/000,218, Non Final Office Action dated Jan. 10, 2022, 23 pgs.

U.S. Appl. No. 17/000,218, Preliminary Amendment filed Nov. 2, 2021, 7 pgs.

U.S. Appl. No. 17/000,218, Response filed Jun. 10, 2022 to Non Final Office Action dated Jan. 10, 2022, 9 pgs.

European Application Serial No. 21192254.7, Extended European Search Report dated Jan. 24, 2022, 8 pgs.

\* cited by examiner

SYSTEMS, METHODS, AND DEVICES FOR SLEEP INTERVENTION QUALITY ASSESSMENT

TECHNICAL FIELD

The present disclosure relates to mechanisms and processes directed to measurements of brain activity and sleep intervention quality assessment.

BACKGROUND

Human sleep can be measured using several aspects of the human physiology including their brain activity, their heart activity, their eye activity, temperature, movement, oxygen saturation, and the like. A human brain may include neurons which exhibit measurable electrical signals when active. Accordingly, various measuring modalities, such as electrodes, may be used to measure such electrical activity. The neural activity of neurons may include many a variety of frequency components. Accordingly, such electrical activity may be measured and represented as a power spectrum in a frequency domain. Moreover, such measurements may be obtained as a user sleeps. Similarly, other measurements may be obtained, such as heart rate activity that includes a heart rate (mean, minimum or maximum over a period, mean square over a period), as well as heart rate variability (beat-to-beat, or beat-to-beat aggregated over a window of time). However, traditional techniques for measuring such electrical activity in such contexts remain limited in their ability to utilize such measurements, and more specifically, to efficiently and effectively assess the efficacy of sleep intervention strategies and techniques.

SUMMARY

Provided are systems, methods, and devices for sleep intervention quality assessment. Methods include receiving measurement data from a plurality of data sources, the measurement data comprising a plurality of measurements of biological parameters of a user before and after a sleep intervention, and receiving treatment data comprising one or more treatment parameters associated with the sleep intervention. Methods further include generating, using one or more processors, a plurality of quality assessment metrics based on the received measurement data, the plurality of quality assessment metrics being generated based, at least in part, on a comparison of the plurality of measurements of biological parameters before and after the sleep intervention, and generating a report based, at least in part, on the plurality of quality assessment metrics.

In some embodiments, methods further include generating a plurality of additional measurements based, at least in part, on the received measurement data. In various embodiments, the plurality of additional measurements represents a plurality of biomarkers associated with the user. According to some embodiments, each of the plurality of quality assessment metrics represents a comparison of a measured performance against a reference value. In some embodiments, each of the plurality of quality assessment metrics is associated with at least one of the plurality of biomarkers. In various embodiments, the report is capable of being displayed as a user interface screen in a display device. According to some embodiments, the methods further include receiving one or more inputs from the user via the user interface screen, and configuring the report based, at least in part, on the received one or more inputs. According to some embodiments, the methods further include generating an estimation model based, at least in part, on the received measurement data, the estimation model being configured to generate one or more predicted results associated with a selected intervention treatment. In some embodiments, the treatment data is received from a plurality of different data sources.

Systems include a communications interface configured to receive measurement data from a plurality of data sources, the measurement data comprising a plurality of measurements of biological parameters of a user before and after a sleep intervention, the communications interface being further configured to receive treatment data comprising one or more treatment parameters associated with the sleep intervention. Systems also include a processing device comprising one or more processors configured to generate a plurality of quality assessment metrics based on the received measurement data, the plurality of quality assessment metrics being generated based, at least in part, on a comparison of the plurality of measurements of biological parameters before and after the sleep intervention, the processing device further configured to generate a report based, at least in part, on the plurality of quality assessment metrics\. Systems further include a memory device configured to store the plurality of quality assessment metrics and the report.

In some embodiments, the processing device is further configured to generate a plurality of additional measurements based, at least in part, on the received measurement data, and the plurality of additional measurements represents a plurality of biomarkers associated with the user. In various embodiments, each of the plurality of quality assessment metrics represents a comparison of a measured performance against a reference value, and each of the plurality of quality assessment metrics is associated with at least one of the plurality of biomarkers. According to some embodiments, the report is capable of being displayed as a user interface screen in a display device. In some embodiments, the processing device is further configured to receive one or more inputs from the user via the user interface screen, and configure the report based, at least in part, on the received one or more inputs. In some embodiments, the processing device is further configured to generate an estimation model based, at least in part, on the received measurement data, the estimation model being configured to generate one or more predicted results associated with a selected intervention treatment.

Also disclosed herein are devices that include a communications interface configured to receive measurement data from a plurality of data sources, the measurement data comprising a plurality of measurements of biological parameters of a user before and after a sleep intervention, the communications interface being further configured to receive treatment data comprising one or more treatment parameters associated with the sleep intervention. The devices further include a processing device comprising one or more processors configured to generate a plurality of quality assessment metrics based on the received measurement data, the plurality of quality assessment metrics being generated based, at least in part, on a comparison of the plurality of measurements of biological parameters before and after the sleep intervention, the processing device further configured to generate a report based, at least in part, on the plurality of quality assessment metrics.

In some embodiments, the processing device is further configured to generate a plurality of additional measurements based, at least in part, on the received measurement data, and the plurality of additional measurements represents a plurality of biomarkers associated with the user. In various embodiments, each of the plurality of quality assessment metrics represents a comparison of a measured performance against a reference value, and each of the plurality of quality assessment metrics is associated with at least one of the plurality of biomarkers. According to some embodiments, the report is capable of being displayed as a user interface screen in a display device. In some embodiments, the processing device is further configured to generate an estimation model based, at least in part, on the received measurement data, the estimation model being configured to generate one or more predicted results associated with a selected intervention treatment.

This and other embodiments are described further below with reference to the figures.

DETAILED DESCRIPTION OF EXAMPLE EMBODIMENTS

Reference will now be made in detail to some specific examples including the best modes contemplated by the inventors. Examples of these specific embodiments are illustrated in the accompanying drawings. While the present disclosure is described in conjunction with these specific embodiments, it will be understood that it is not intended to limit the disclosure to the described embodiments. On the contrary, it is intended to cover alternatives, modifications, and equivalents as may be included within the spirit and scope of the disclosure as defined by the appended claims. In addition, although many of the components and processes are described below in the singular for convenience, it will be appreciated by one of skill in the art that multiple components and repeated processes can also be used to practice the techniques of the present disclosure.

In the following description, numerous specific details are set forth in order to provide a thorough understanding of the present invention. Particular embodiments may be implemented without some or all of these specific details. In other instances, well known process operations have not been described in detail in order not to unnecessarily obscure the disclosure.

Figure 1:
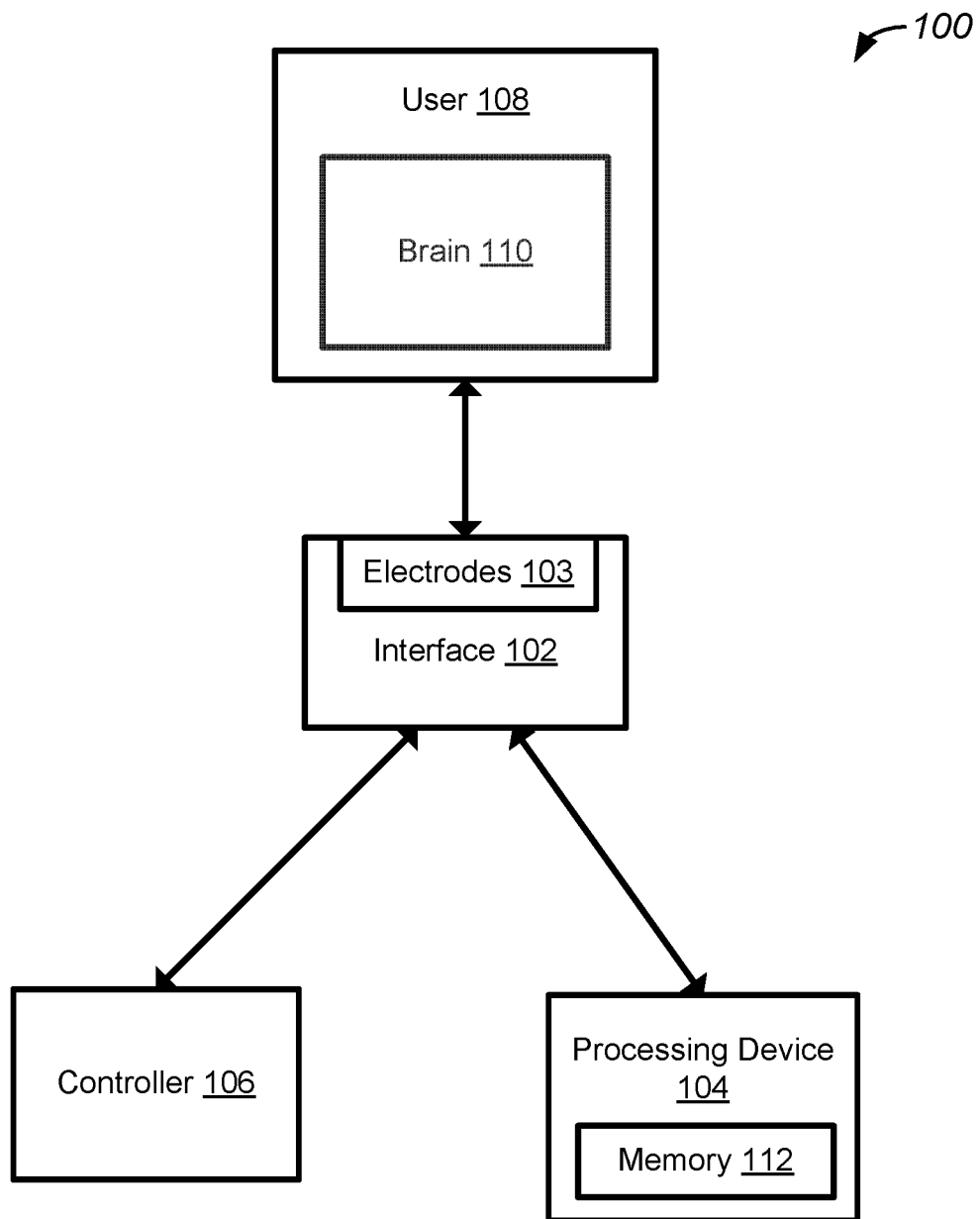
FIG. 1 illustrates an example of a system for sleep intervention quality assessment, configured in accordance with some embodiments.

FIG. 1 illustrates an example of a system for sleep intervention quality assessment, configured in accordance with some embodiments. As will be discussed in greater detail below, a user may undergo sleep interventions that are intended to enhance and improve a user's sleep. Embodiments disclosed herein enable the identification and generation of sleep quality metrics to assess an efficacy of such treatment modalities.

As will be discussed in greater detail below, components of system 100 may be implemented to provide assessment of sleep interventions of a user, such as user 108. As shown in FIG. 1, user 108 may be a person, and may be coupled to components of system 100. More specifically, brain 110 of user 108 may be coupled to system 100 such that system 100 is able to monitor and measure neural activity within brain 110. In some embodiments, the activity is electrical activity that is measured and recorded as electrical measurements. In this way, activity within brain 110 may be monitored during a period of sleep. As will also be discussed in greater detail below, the coupling between user 108 and system 100 may also enable stimulation of neurons within brain 110. Accordingly, system 100 may also modify neural activity of user 108.

In various embodiments, coupling between user 108 and system 100 may be implemented, at least in part, via an interface, such as interface 102. In one example, interface 102 includes a plurality of electrodes. More specifically, such electrodes may be implemented as an electrode array. Such electrodes may be included in a scalp potential electroencephalogram (EEG) array, may be deep brain stimulation (DBS) electrodes such as electrodes used with intracranial electroencephalography, or may be an epidural grid of electrodes. In other examples, the electrodes may include optogenetics mechanisms for monitoring various neuronal processes or blood saturation. Mechanisms may be used to make various measurements and acquire measurement signals corresponding to neural activity, heart activity, temperature, body/head/eye movements. As used herein, neural activity may refer to spiking or non-spiking activity/potentiation. Moreover, heart activity may be a measure of beat rate or beat-to-beat variability. Furthermore, eye movements may include micro and macro saccades, as well as slow and rapid eye movements.

In various embodiments, such measured signals may be electrical signals derived based on neural activity that may occur in cortical tissue of a brain or may include electrical and optical signals derived from the peripheral parts of the user. Such measurements may be acquired and represented in a time domain and/or frequency domain. In this way, activity may be monitored and measured over one or more temporal windows, and such measurements may be stored and utilized by system 100. In various embodiments, such neural activity may be observed for particular regions of cortical tissue determined, at least in part, based on a configuration of interface 102. In one example, this may be determined based on a configuration and location of electrodes included in interface 102 and coupled with the brain.

According to some embodiments, one or more components of interface 102 are configured to provide stimuli to the brain coupled with interface 102. For example, one or more electrodes included in interface 102 may be configured to provide electrical stimuli to cortical tissue of the brain. As discussed above, such electrodes may be implemented utilizing one or more of various modalities which may be placed on a user's scalp, or implanted in the user's brain.

As will be discussed in greater detail below, such actuation and stimuli provided by interface 102 may be of many different modalities. For example, stimuli may be aural, visual, and/or tactile as well as being electrical and/or magnetic, or any suitable combination of these. Accordingly, interface 102 may further includes additional components, such as speakers, lights, display screens, and mechanical actuators that are configured to provide one or more of aural, visual, and/or tactile stimuli to a user. In this way, any suitable combination of different modalities may be used. For example, a combination of electrical and aural stimuli may be provided via interface 102. Further still, interface 102 may include different portions corresponding to signal acquisition and stimuli administration. For example, a first portion of interface 102 may include electrodes configured to measure neural activity, while a second portion of interface 102 includes speakers configured to generate aural stimuli. In another example, a third portion of interface 102 may include electrodes to measure ECG or heart rate, while a fourth portion may include sensors to measure oxygen saturation.

In some embodiments, interface 102 further includes one or more dedicated processors and an associated memory configured to obtain and store the measurements acquired at interface 102. In this way, such measurements may be stored and made available to other system components which may be communicatively coupled with interface 102.

System 100 further includes processing device 104 which may be configured to receive measurements made by interface 102, and may be further configured to assess the efficacy of sleep interventions applied to user 108. As will be discussed in greater detail below, the assessment of the efficacy of sleep interventions may be made based on received measurement data and treatment data which may be used to generate a plurality of quality assessment metrics. Accordingly, processing device 104 is configured to retrieve measurement data from one or more data sources, which may be a memory device or a database system, and is further configured to retrieve measurement data obtained from the user. Processing device 104 is further configured to generate a plurality of quality assessment metrics based on the received measurement data and treatment data.

Moreover, in some embodiments, processing device 104 is further configured to generate a result object, such as a report, that provides a summary of the quality assessment metrics. In various embodiments, the report is included in a data object capable of being displayed in a user interface screen. In some embodiments, processing device 104 is further configured to generate a user interface, such as a control panel, that is configured to display an output to a user, and receive an input form the user via one or more data fields. In this way, the user may be provided with a report which may be configurable via the user interface. In various embodiments, the control panel may also include various user interface objects which may be configured to receive inputs form the user. Accordingly, the control panel may be configured to include various data fields and drop-down menus that may enable a user to provide inputs to processing device 104, and configure the implementation of the quality assessment metrics, the generation of result objects, as well as the implementation sleep intervention modalities. In this way the control panel is configured to provide the user with extensive configurability of system 100.

As will also be discussed in greater detail below, processing device 104 may be further configured to generate one or more recommendations associated with the treatment or intervention strategy, and such recommendations may be included in the user interface screen. In some embodiments, processing device 104 includes memory device 112 which is configured to store quality assessment metrics and result objects, such as reports, generated by processing device 104.

In some embodiments, system 100 includes controller 106 which is configured to generate one or more control signals for interface 102, and is also configured to receive measurements from interface 102. Accordingly, controller 106 may be configured to implement and control the application of one or more sleep intervention modalities. In various embodiments, controller 106 is communicatively coupled with interface 102, and processing device 104. Accordingly, controller 106 is configured to received inputs from various other system components, and generate signals provided to interface 102 based, at least in part on such inputs. As will be discussed in greater detail below, such outputs may be used to provide actuations to the brain coupled with interface 102. For example, outputs generated by controller 106 may be used to stimulate the brain via one or more components of interface 102. In this way, controller 106 may provide stimuli to the brain via interface 102, may receive sleep information via other components such as processing device 104, and may generate stimuli based on such received information.

In some embodiments, controller 106 is configured to implement combined control of pharmacological and stimulation inputs. Accordingly, controller 106 may be configured to modify stimulation inputs based on an expected effect of one or more pharmacological agents that may be administered in conjunction with the stimulation. In this way, controller 106 may modify and control administration of stimuli via interface 102 based on an identified pharmacological regimen. In various embodiments, controller 106 is optionally included in system 100. For example, system 100 might not include controller 106, and such generation of control signals and receiving of measurements may be implemented by processing device 104.

Figure 2:
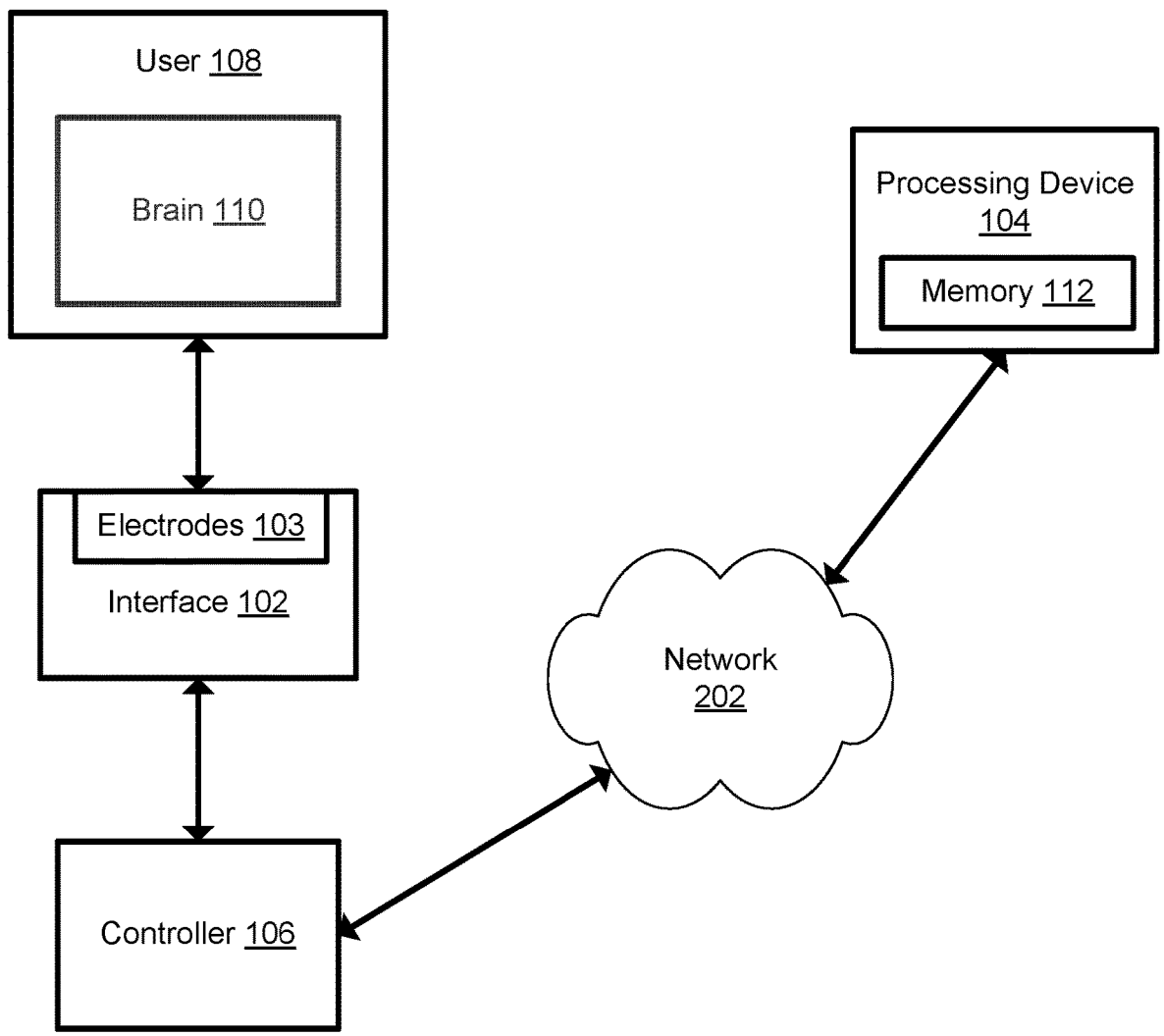
FIG. 2 illustrates another example of a system for sleep intervention quality assessment, configured in accordance with some embodiments.

FIG. 2 illustrates another example of a system for sleep intervention quality assessment, configured in accordance with some embodiments, configured in accordance with some embodiments. As similarly discussed above, a user may undergo sleep interventions that are intended to enhance and improve a user's sleep. Moreover, systems, such as system 200, may include components such as interface 102, processing device 104, and controller 106, which may be coupled to a user, such as user 108.

As shown in FIG. 2, components of system 200 may be implemented in a distributed manner. For example, controller 106 may be collocated with user 108 and may be communicatively coupled to processing device 104 via a communications network, such as network 202. In this way, controller 106 may be implemented as a wireless device, such as a wearable device, at user 108, processing device 104 may be implemented remotely in a data processing system, and communications between controller 106 and processing device 104 may be handled via a network 202, which may be the internet. In this way, processing device 104 may be implemented as a personal computer or mobile device located near user 108, or processing device may be implemented as part of a distributed computing platform configured to provide sleep profile enhancement as a Software as a Service (Saas) platform.

Figure 3:
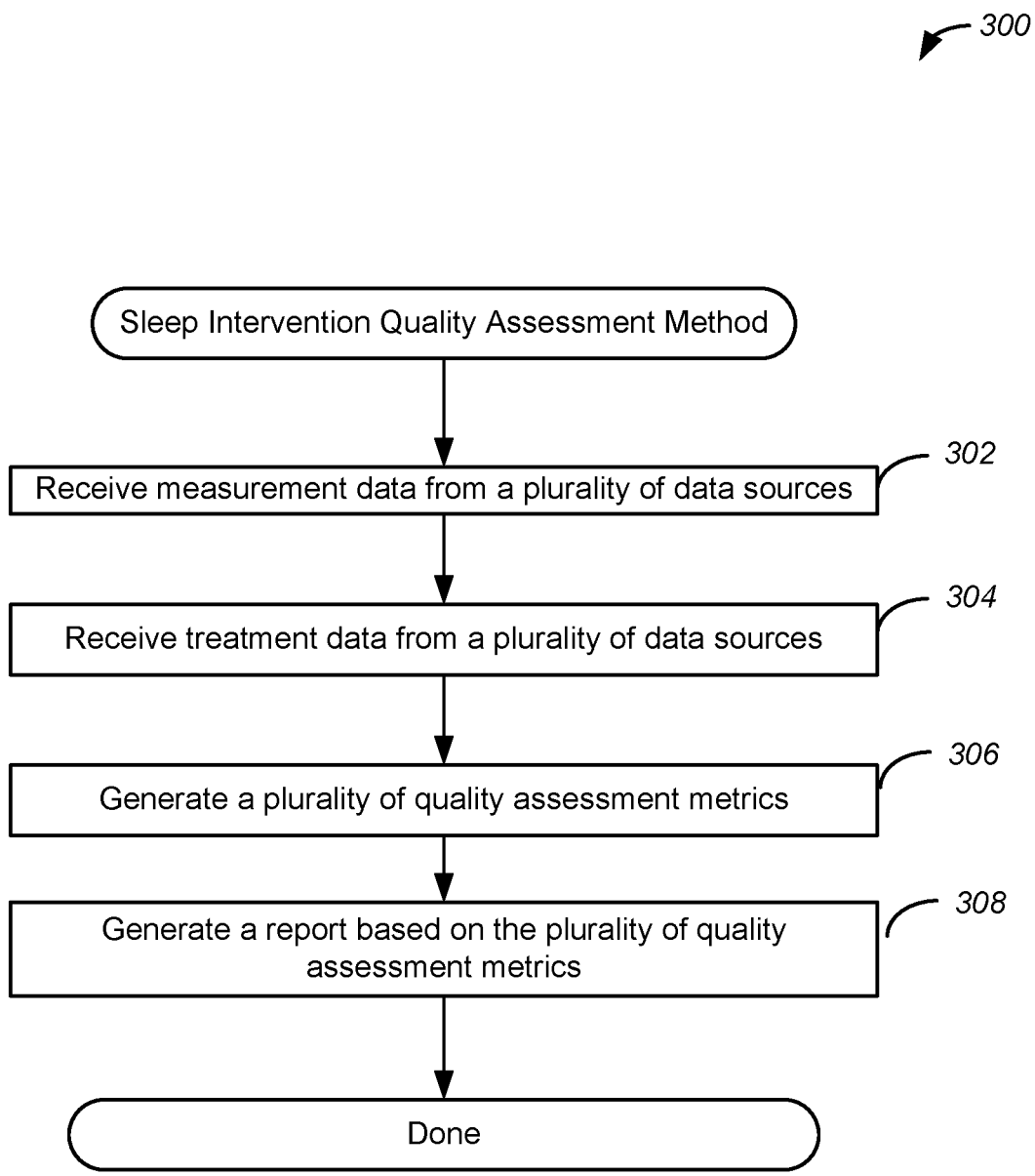
FIG. 3 illustrates an example of a flow chart of a method for sleep intervention quality assessment, implemented in accordance with some embodiments.

FIG. 3 illustrates an example of a flow chart of a method for sleep intervention quality assessment, implemented in accordance with some embodiments. As similarly discussed above, a user may undergo sleep interventions that are intended to enhance and improve a user's sleep. As will be discussed in greater detail below, treatment data may be retrieved and analyzed in combination with a user's measured sleep data to formulate quality assessment metrics that represent a quality of the treatment or intervention.

Accordingly, method 300 may commence with operation 302 during which measurement data may be received from a plurality of data sources. In various embodiments, the measurement data includes measurements of various biological parameters of the user before and after a sleep intervention. As discussed above, such measurements may be made via system components, such as electrodes, and may be recorded and stored as measurement data. Moreover, as will be discussed in greater detail below, the raw measurement data may be pre-processed to generate one or more additional measurements, such as biomarkers.

Method 300 may proceed to operation 304 during which treatment data may be received. In various embodiments, the treatment data may include one or more data values representing a particular sleep intervention that has been utilized. For example, such treatment data may include stimulation parameters used to apply the stimuli to the user. In another example, the treatment data may include pharmacological data representing doses of pharmacological treatments given to the user. In this way, the treatment data may include data representing various different treatment modalities for a particular user.

Method 300 may proceed to operation 306 during which a plurality of quality assessment metrics may be generated. In various embodiments, the plurality of quality assessment metrics is generated based, at least in part, on a comparison of the plurality of measurements before and after the sleep intervention. Accordingly, during operation 302, the received measurement data may have included various historical data for the user. During operation 306, measurement data from before a treatment may be compared against measurement data from after a treatment to generate quality assessment metrics that assess a quality and efficacy of the treatment on the user.

Method 300 may proceed to operation 308 during which a report may be generated based on the quality assessment metrics. Accordingly, the report may include a summary of the results, and the report may be displayed in a user interface screen. As will be discussed in greater detail below, the report may also include various recommendations for sleep interventions as well as predictions associated with sleep interventions.

Figure 4:
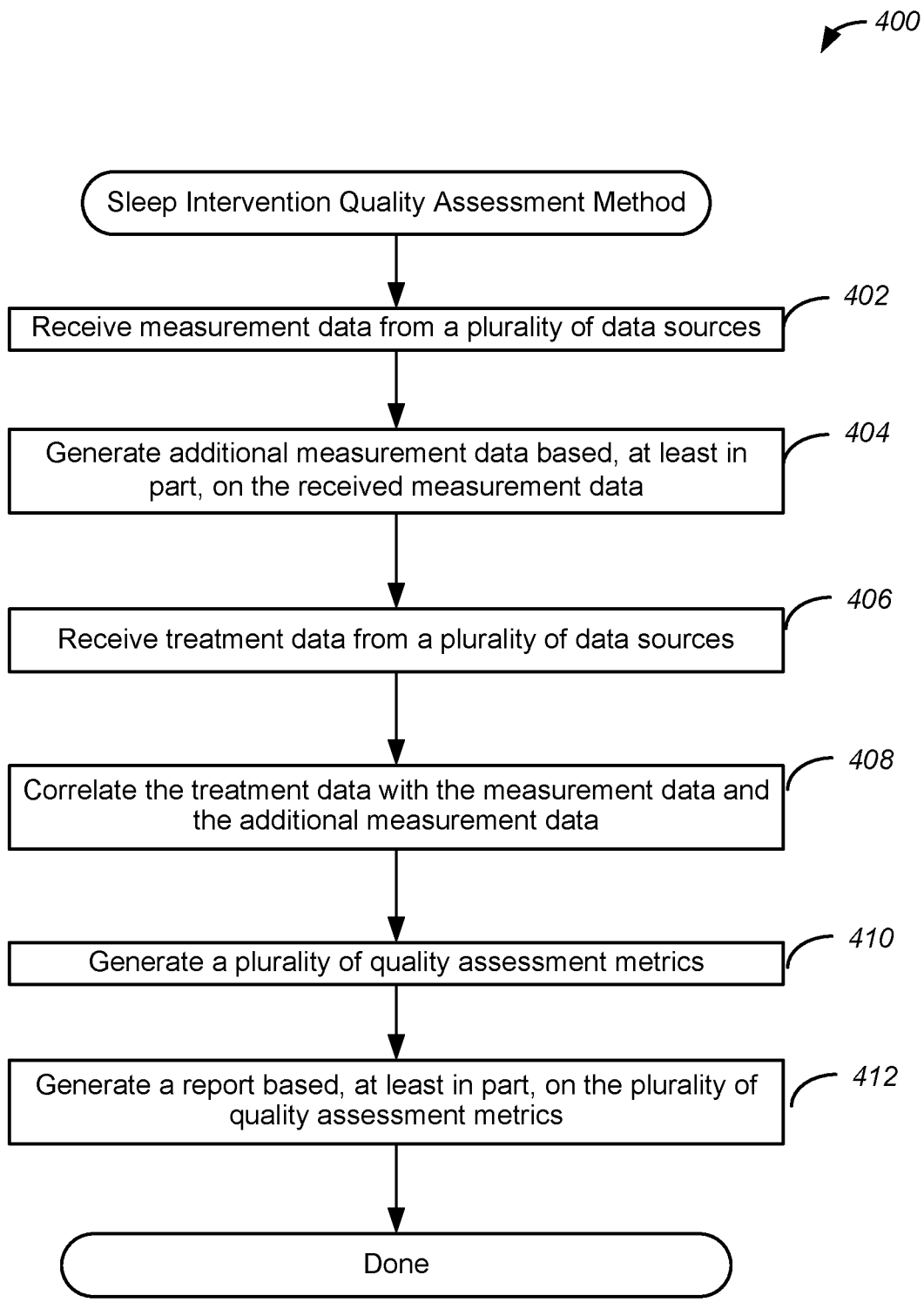
FIG. 4 illustrates another example of a flow chart of a method for sleep intervention quality assessment, implemented in accordance with some embodiments.

FIG. 4 illustrates another example of a flow chart of a method for sleep intervention quality assessment, implemented in accordance with some embodiments. As similarly discussed above, a user may undergo sleep interventions and/or interventions that are intended to enhance and improve a user's sleep. As will be discussed in greater detail below, treatment data may be retrieved and analyzed in combination with a user's measured sleep data to formulate quality assessment metrics that represent a quality of the treatment or intervention.

Accordingly, method 400 may commence with operation 402 during which measurement data may be received from a plurality of data sources. As discussed above, the measurement data includes measurements of various biological parameters of the user before and after a sleep intervention. Furthermore, the measurement data may be raw data obtained via system components, such as electrodes, and may be stored in memory as measurement data. In some embodiments, the measurement data may also include self-reported measures of the sleep, relaxation, alertness, emotional state, and insomnia level.

Method 400 may proceed to operation 404 during which the measurement data may be pre-processed to generate additional measurement data. As noted above, such additional measurement data may include the representation of one or more biomarkers of the user. As disclosed herein, such biomarkers may be used to identify markers of a user's sleep profile. Accordingly, during operation 404 amplitudes and frequency spectra of the raw measurement data may be analyzed to generate additional measurement data that includes various biomarkers. For example, biomarkers may include parameters of individualized exponential curve fits to a user's spectral data before, during, and after sleep, as well as during each of the different stages of sleep. In some embodiments, biomarkers may include specific power band ratios (for example the delta power over beta power, slow wave power over beta power, or slow wave power over low beta power). The biomarkers also include specific resonant frequencies and changes in the resonant frequencies for the user before, during, and after sleep, as well as during the different stages of the sleep. In some embodiments, the biomarkers include a representation of absolute or relative power distribution in the different spectral bins/bands for each time period of interest, which may be configured to be specific time windows before and/or after sleep, or specific sleep stages, or overall NREM sleep and REM sleep stages.

In various embodiments, the progression of these biomarkers over the user's sleep cycle, starting with pre-sleep, through sleep, and after sleep, may be used to represent and define a sleep profile for the user. Accordingly, the sleep profile may store the values of the biomarkers, as well as difference values identifying changes in such biomarkers. Moreover, the biomarkers and sleep profiles may be aggregated for a group of users, and deviations from the group measurement could be a reported metric. Additional biomarkers derived from the measurements may include the heart rate based biomarkers like heart rate (HR) or heart rate variability (HRV) measures that may also be included in an evolving sleep profile that may represent such values before, after, and during the different sleep stages or as a temporal evolution/time series profile in which measurements are made every few seconds, such as 30 seconds. Other biomarkers may also be generated based on movement measurements that track physical movements of the user. In some embodiments, the additional measurement data may also include a pre-post differential measure of self-reported survey metrics of alertness, relaxation, anxiety, emotional states. As will be discussed in greater detail below, any of the biomarkers discussed above may be used to generate quality assessment metrics.

Method 400 may proceed to operation 406 during which treatment data may be received. As discussed above, the treatment data may include one or more data values representing a particular sleep intervention that has been utilized. Accordingly, the treatment data may include data representing various different treatment modalities for a particular user. In various embodiments, during operation 406, one or more data sources may be queried to obtain the treatment data. For example, and external database system may be queried using a user identifier to obtain treatment data. In another example, a system component, such as a memory device or database, may be queried to obtain the treatment data if it is already available locally. In this way, treatment data may be identified and retrieved for a particular user.

Method 400 may proceed to operation 408 during which the treatment data may be correlated with the measurement data. Accordingly, the treatment data may be associated with particular measurement data. In one example, such correlation and association may be implemented via available metadata, such as timestamp data. For example, treatment data may be received that has a particular time and date included in its metadata. A system component, such as a processing device, may query the available measurement data and retrieve measurement data obtained before, during, and after that identified timestamp. The identification and retrieval of the measurement data may be bounded by a temporal parameter which may be a designated parameter specified by an entity such as the user or an administrator.

Method 400 may proceed to operation 410 during which a plurality of quality assessment metrics may be generated. As similarly discussed above, the plurality of quality assessment metrics is generated based, at least in part, on a comparison of the plurality of measurements before and after the sleep intervention. Accordingly, during operation 410, measurement data from before a treatment may be compared against measurement data from after a treatment to generate quality assessment metrics that assess a quality and efficacy of the treatment on the user.

In various embodiments, such quality assessment metrics may be metrics that represent a measured performance compared against a reference value. Accordingly, a system component may have previously retrieved reference data that represents an ideal result of a treatment. In various embodiments, the actual measured result of the treatment may be compared against the reference value, and a quality assessment metric may be generated that represents the comparison. For example, the quality assessment metric may be a number computed based on a ratio between the measured value and the reference value. Such computations may be performed for multiple dimensions of the measurement data, and may thus be computed for various different biological parameters and biomarkers of the user.

For example, the reference value could be generated based on aggregated measurement data from large groups of users. The reference value could also include age specific variations in measurements that have been obtained from a statistical distribution. The reference value could additionally include other demographic attributes identified based reference distributions (including gender, ethnicity, as well as health conditions, such as insomnia severity index). In some embodiments, the treatment conditions could identify specific measurements to prioritize. For example, if there is an electrical stimulation of specific frequency used as treatment, spectral measurements in and around that specific frequency band could be prioritized for the generation of a quality assessment metric. In other instances, generalized metrics could be prioritized based on predetermined rules of sleep quality improvement, such as enhancement in slow wave activity, or suppression of high frequency activity. In some embodiments, these measurements may be collated over multiple treatment/sleep sessions, and used to generate a baseline reference specific to a user, and the quality assessment metrics may be measured relative to the user's baseline.

Method 400 may proceed to operation 412 during which a report may be generated based on the quality assessment metrics. As similarly discussed above, the report may include a summary of the results, and the report may be displayed in a user interface screen. Accordingly, the report may be a data object capable of being displayed in a user interface, and including various configurable data fields that are configured to display the computed quality assessment metrics. In some embodiments, the report further includes hyperlinks which are custom generated and configured to link to data objects including the underlying data. In this way, the report may further provide linking to other data objects that may additionally be used to assess the quality of a particular sleep intervention.

Figure 5:
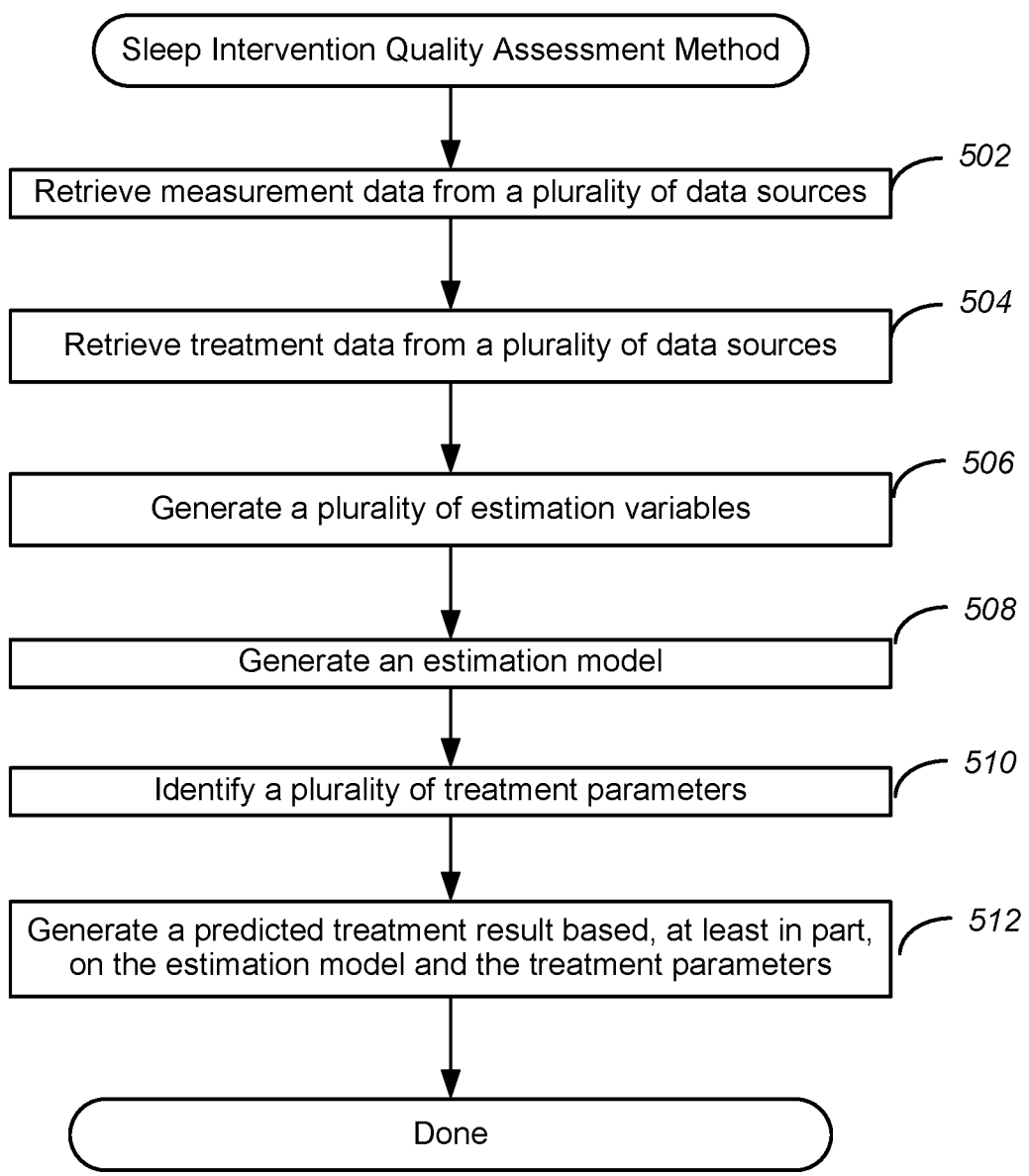
FIG. 5 illustrates an additional example of a flow chart of a method for sleep intervention quality assessment, implemented in accordance with some embodiments.

FIG. 5 illustrates an additional example of a flow chart of a method for sleep intervention quality assessment, implemented in accordance with some embodiments. As will be discussed in greater detail below, a user may undergo sleep interventions that are intended to enhance and improve a user's sleep. As also discussed above, sleep quality metrics may be generated to assess an efficacy of such treatment modalities. As will also be discussed in greater detail below, embodiments disclosed herein are further configured to implement a predictive model that may be used to provide an estimation of a result of a treatment.

Accordingly, method 500 may commence with operation 502 during which measurement data may be retrieved. As discussed above, the measurement data includes measurements of various biological parameters of the user before and after a sleep intervention. Furthermore, the measurement data may be raw data obtained via system components, such as electrodes, and may be stored in memory as measurement data. As also discussed above, the measurement data may be pre-processed to generate additional measurement data.

Method 500 may proceed to operation 504 during which treatment data may be retrieved. As discussed above, the treatment data may include one or more data values representing a particular sleep intervention that has been utilized. Accordingly, the treatment data may include data representing various different treatment modalities for a particular user. As also discussed above, one or more data sources may be queried to obtain the treatment data. For example, an external database system may be queried using a user identifier to obtain treatment data. In another example, a system component, such as a memory device or database, may be queried to obtain the treatment data if it is already available locally.

Method 500 may proceed to operation 506 during which estimation variables may be generated. In various embodiments, the estimation variables represent the different variables that will be modeled by an estimation model, discussed in greater detail below. Accordingly, during operation 506, estimation variables may be identified for each biological parameter that is to be modeled. For example, if the estimation model is to provide a prediction for a particular biomarker, that biomarker may be identified as an estimation variable. In various embodiments, such estimation variables may be identified based, at least in part, on one or more designated parameters specified by a user or an administrator during a configuration process. In some embodiments, the estimation variables include any of the sleep quality assessment metrics as discussed above.

Method 500 may proceed to operation 508 during which an estimation model may be generated. Accordingly, during operation 508, an estimation model may be generated that is configured to model a user's response to one or more stimuli in accordance with one or more treatments. The estimation model may be generated using machine learning techniques. For example, previous treatment data and measurement data may be used as training data that trains the machine learning algorithm to simulate the response characteristics of the user's brain. In this way, an estimation model may be generated that is specific to the user, and is configured based on the user's previous measurement and treatment data. In some embodiments, the estimation model can include functional or phenomenological input-output models that may be generated based on machine learning algorithms (such as multi-variate regression, support vector machines, classifiers, deep learning neural networks, hierarchical Bayesian techniques) that are trained to learn the underlying neural behavior. For example, previous measurement data may be used to train these models. Moreover, inputs to these models may be the physiological measurements (like the electrical activity, heart activity, EOG, movement), self-reported measurements, and the treatment parameters (such as stimulation modality, the specific stimulation parameters like intensity, and frequency). As will be discussed in greater detail below, inverse models may also be generated that may be used to estimate various stimulation and treatment parameters based on a specified target user response.

Method 500 may proceed to operation 510 during which treatment parameters may be identified. In various embodiments, such treatment parameters may represent an input that is to be provided to the estimation model. The treatment parameters may be selected by a user via the user interface, or may have been inferred from previous treatment data. For example, previous treatment parameters received in treatment data may be selected as treatment parameters to be provided to the model to provide an estimation of what another round of a treatment may cause. In some embodiments, an inverse model may also be generated based on the above estimation models. Such inverse models may be configured to predict the various treatment parameters from a particular sleep assessment metric that is desired. Accordingly, these inverse models (which could also be personalized using data specific to the user and obtained from multiple sessions) may be used to set desired or target values of sleep quality metrics, and estimate the treatment parameters to achieve those target values.

Method 500 may proceed to operation 512 during which a predicted treatment result may be generated. Accordingly, the estimation model may generate an output, and the output may be included in a result object. As similarly discussed above, such a result object may be capable of being display in a user interface, and one or more inputs may be received from the user via the user interface. In this way, the user may be provided with various estimations of the results of different treatment modalities.

Figure 6:
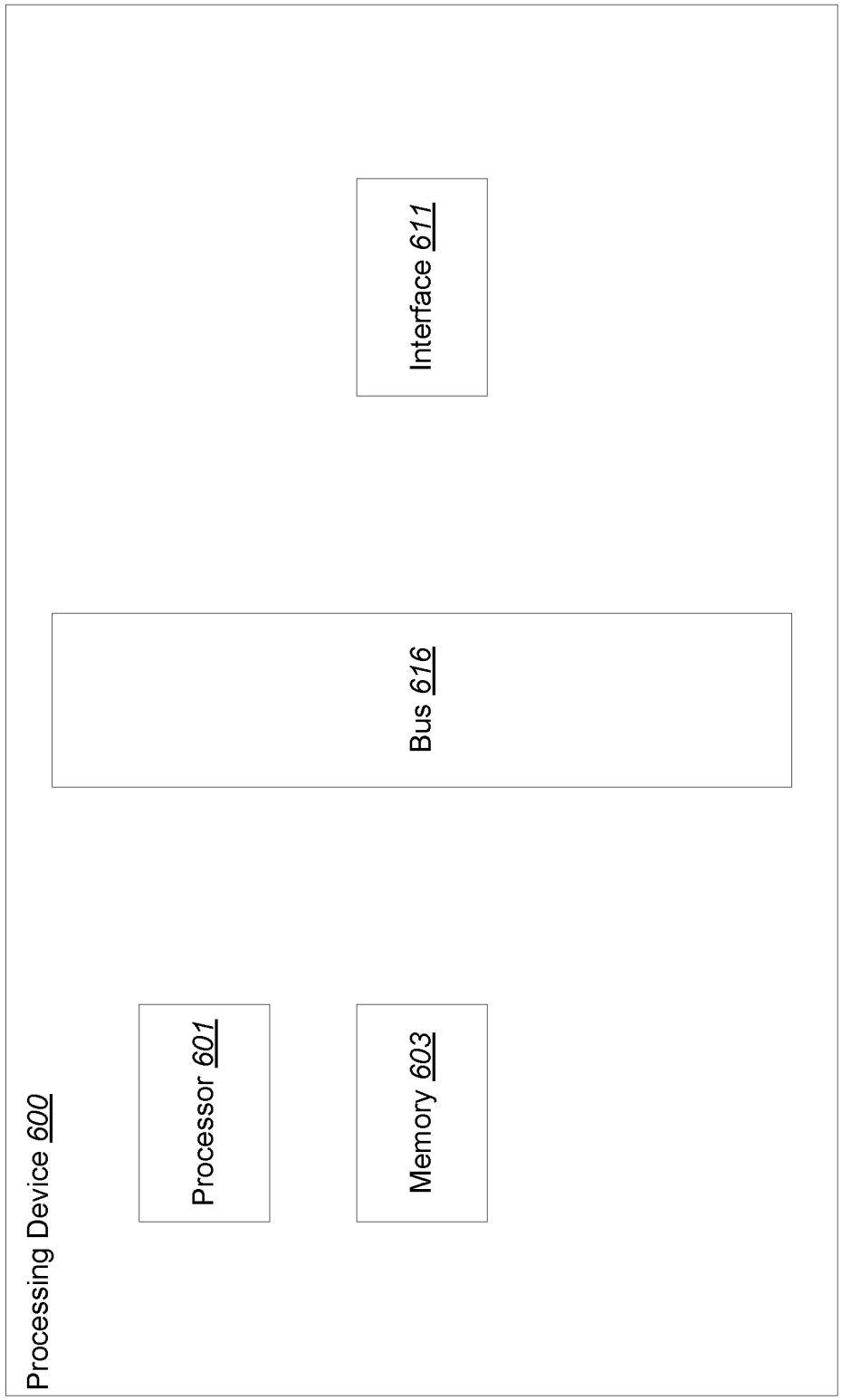
FIG. 6 illustrates an example of a processing device that can be used with various embodiments.

FIG. 6 illustrates an example of a processing device that can be used with various embodiments. For instance, the processing device 600 can be used to implement any of processing device 104 and controller 106 according to various embodiments described above. In addition, the processing device 600 shown can be implemented in conjunction with a computing system on a mobile device or on a computer or laptop, etc. According to particular example embodiments, a processing device 600 suitable for implementing particular embodiments of the present invention includes a processor 601, a memory 603, an interface 611, and a bus 616 (e.g., a PCI bus). The interface 611 may include separate input and output interfaces, or may be a unified interface supporting both operations. When acting under the control of appropriate software or firmware, the processor 601 is responsible for tasks such as quality assessment metric computation and generation. Various specially configured devices can also be used in place of a processor 601 or in addition to processor 601. The complete implementation can also be done in custom hardware. The interface 611 may be configured to send and receive data packets or data segments over a network. Particular examples of interfaces the device supports include Ethernet interfaces, frame relay interfaces, cable interfaces, DSL interfaces, token ring interfaces, and the like. In various embodiments, interface 611 may also be a wired connection or a bus with appropriate communications ports.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the processing device 600 uses memory 603 to store data and program instructions and maintain a local side cache. The program instructions may control the operation of an operating system and/or one or more applications, for example. The memory or memories may also be configured to store received metadata and batch requested metadata.

Because such information and program instructions may be employed to implement the systems/methods described herein, the present invention relates to tangible, machine readable media that include program instructions, state information, etc. for performing various operations described herein. Examples of machine-readable media include memory devices such as non-volatile memory devices, volatile memory devices, and may also utilize optical media such as CD-ROM disks and DVDs, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

While the present disclosure has been particularly shown and described with reference to specific embodiments thereof, it will be understood by those skilled in the art that changes in the form and details of the disclosed embodiments may be made without departing from the spirit or scope of the disclosure. Specifically, there are many alternative ways of implementing the processes, systems, and apparatuses described. It is therefore intended that the invention be interpreted to include all variations and equivalents that fall within the true spirit and scope of the present invention. Moreover, although particular features have been described as part of each example, any combination of these features or additions of other features are intended to be included within the scope of this disclosure. Accordingly, the embodiments described herein are to be considered as illustrative and not restrictive.

What is claimed is:

1. A method comprising:
receiving measurement data from a plurality of data sources, the measurement data comprising a plurality of measurements of biological parameters of the user before and after a sleep intervention;
receiving treatment data comprising one or more treatment parameters associated with the sleep intervention;
generating, using one or more processors, a plurality of quality assessment metrics based on the received measurement data, the plurality of quality assessment metrics being generated based, at least in part, on a comparison of the plurality of measurements of biological parameters before and after the sleep intervention and a comparison of a plurality of biomarkers identifying markers in a sleep profile of the user;
training a machine learning estimation model based, at least in part, on the plurality of quality assessment metrics and the received treatment data, the estimation model being configured to generate one or more predicted results associated with one or more estimation variables associated with one or more intervention treatments, the one or more estimation variables including one or more of the plurality of quality assessment metrics;

generating an inverse model, the inverse model configured to estimate one or more treatment parameters to achieve a target value of a selected quality assessment metric of the plurality of assessment metrics; and providing the one or more treatment parameters to the machine-learning estimation model to provide an estimation of a result of another round of the sleep intervention.

2. The method of claim 1 further comprising:
generating a plurality of additional measurements based, at least in part, on the received measurement data.

3. The method of claim 2, wherein the plurality of additional measurements represents the plurality of biomarkers associated with the user.

4. The method of claim 3, wherein each of the plurality of quality assessment metrics represents a comparison of a measured performance against a reference value.

5. The method of claim 4, wherein each of the plurality of quality assessment metrics is associated with at least one of the plurality of biomarkers.

6. The method of claim 1, further comprising generating a report based, at least in part, on the estimation model, wherein the report is capable of being displayed as a user interface screen in a display device.

7. The method of claim 6 further comprising:
receiving one or more inputs from the user via the user interface screen; and
configuring the report based, at least in part, on the received one or more inputs.

8. The method of claim 1, wherein the treatment data is received from a plurality of different data sources.

9. The method of claim 1, wherein a subset of the measurement data from a plurality of data sources is prioritized in the generation of the plurality of quality assessment metrics.

10. The method of claim 9, wherein the prioritization is based on a frequency band, enhancement in slow wave activity, or suppression of high frequency activity.

11. The method of claim 1, wherein the actuations include at least one of aural, visual, tactile, electrical or magnetic.

12. The method of claim 1, wherein the sleep intervention includes providing pharmacological input to the user.

13. The method of claim 1, wherein the sleep intervention is applied to the user is via electrodes.

14. A system comprising:
one or more computer processors;
one or more computer memories;
a set of instructions stored in the one or more computer memories, the set of instructions configuring the one or more computer processors to perform operations, the operations comprising:
receiving measurement data from a plurality of data sources, the measurement data comprising a plurality of measurements of biological parameters of the user before and after the sleep intervention;
receiving treatment data comprising one or more treatment parameters associated with the sleep intervention;
generating a plurality of quality assessment metrics based on the received measurement data, the plurality of quality assessment metrics being generated based, at least in part, on a comparison of the plurality of measurements of biological parameters before and after the sleep intervention and a comparison of a plurality of biomarkers identifying markers in a sleep profile of the user;
training a machine learning estimation model based, at least in part, on the plurality of quality assessment metrics and the received treatment data, the estimation model being configured to generate one or more predicted results associated with one or more estimation variables associated with one or more intervention treatments, the one or more estimation variables including one or more of the plurality of quality assessment metrics;
generating an inverse model, the inverse model configured to estimate one or more treatment parameters to achieve a target value of a selected quality assessment metric of the plurality of assessment metrics; and
providing the one or more treatment parameters to the machine-learning estimation model to provide an estimation of a result of another round of the sleep intervention.

15. The system of claim 14, the operations further comprising generating a plurality of additional measurements based, at least in part, on the received measurement data, and wherein the plurality of additional measurements represents the plurality of biomarkers associated with the user.

16. The system of claim 15, wherein each of the plurality of quality assessment metrics represents a comparison of a measured performance against a reference value, and wherein each of the plurality of quality assessment metrics is associated with at least one of the plurality of biomarkers.

17. The system of claim 14, the operations further comprising generating a report based, at least in part, on the estimation model, wherein the report is capable of being displayed as a user interface screen in a display device.

18. The system of claim 17, the operations further comprising:
receiving one or more inputs from the user via the user interface screen; and
configuring the report based, at least in part, on the received one or more inputs.

19. A system, comprising:
one or more processors;
at least one electrode configured to apply a sleep intervention including electrical stimulation to a brain of a user; and
one or more non-transitory memories having stored thereon instructions to cause the one or more processors to perform operations, the operations comprising:
receiving measurement data from a plurality of data sources, the measurement data comprising a plurality of measurements of biological parameters of the user before and after the sleep intervention;
receiving treatment data comprising one or more treatment parameters associated with the sleep intervention;
generating a plurality of quality assessment metrics based on the received measurement data, the plurality of quality assessment metrics being generated based, at least in part, on a comparison of the plurality of measurements of biological parameters before and after the sleep intervention and a comparison of a plurality of biomarkers identifying markers in a sleep profile of the user;
training a machine learning estimation model based, at least in part, on the plurality of quality assessment metrics and the received treatment data, the estimation model being configured to generate one or more predicted results associated with one or more estimation variables associated with one or more intervention treatments, the one or more estimation variables including one or more of the plurality of quality assessment metrics;

generating an inverse model, the inverse model configured to estimate one or more treatment parameters to achieve a target value of a selected quality assessment metric of the plurality of assessment metrics and providing the one or more treatment parameters to the machine-learning estimation model to provide an estimation of a result of an additional round of the sleep intervention; and applying the additional round of sleep treatment, the applying of the additional round of the sleep treatment including applying actuations to a brain of the user.

* * * * *